(12) United States Patent
Davis et al.

(10) Patent No.: US 9,623,202 B2
(45) Date of Patent: *Apr. 18, 2017

(54) METHODS FOR USING HEAD POSITIONING PILLOWS TO OPTIMIZE RESPIRATORY TITRATION

(71) Applicant: Banyan Licensing L.L.C., Charlotte, NC (US)

(72) Inventors: Edmund Scott Davis, Clover, SC (US); Antonio Arcieri, Fort Lauderdale, FL (US)

(73) Assignee: BANYAN LICENSING L.L.C., Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/552,243

(22) Filed: Nov. 24, 2014

(65) Prior Publication Data

US 2015/0265793 A1 Sep. 24, 2015

Related U.S. Application Data

(63) Continuation of application No. 12/698,768, filed on Feb. 2, 2010, now abandoned.

(51) Int. Cl.
*A61G 7/07* (2006.01)
*A61M 16/06* (2006.01)
*A47C 20/04* (2006.01)

(52) U.S. Cl.
CPC ......... *A61M 16/0605* (2014.02); *A47C 20/04* (2013.01); *A61G 7/072* (2013.01); *A61M 2205/02* (2013.01); *A61M 2205/58* (2013.01)

(58) Field of Classification Search
CPC .......................................................... A61G 7/07
USPC ..................................... 5/636, 638, 645, 490
See application file for complete search history.

(56) References Cited

U.S. PATENT DOCUMENTS

| 2008/0163428 A1 | 7/2008 | Groteke et al. |
| 2009/0139031 A1* | 6/2009 | Davis ....................... A47G 9/10 |
| | | 5/639 |
| 2011/0185505 A1 | 8/2011 | Davis |

OTHER PUBLICATIONS

IP Australia Patent Office. Australia Patent Examination Report No. 1 dated May 23, 2014. Australia Patent Application No. 2010202994. Name of Applicant: Edmund Scott Davis. English Language. 3 pages.

* cited by examiner

*Primary Examiner* — Fredrick Conley
(74) *Attorney, Agent, or Firm* — Moore & Van Allen PLLC; Henry B. Ward, III

(57) ABSTRACT

Presented herein are various methods for using head positioning pillows to optimize respiratory titration. More specifically, the method includes a first step of determining an optimal relative angle between the patient's mouth and throat at which the patient's airway is optimally opened. The method also includes a second step of adjusting a head positioning pillow relative to the patient's head and neck to modify and transform the configuration of the pillow to achieve a pillow position that achieves the optimal relative angle.

12 Claims, 16 Drawing Sheets

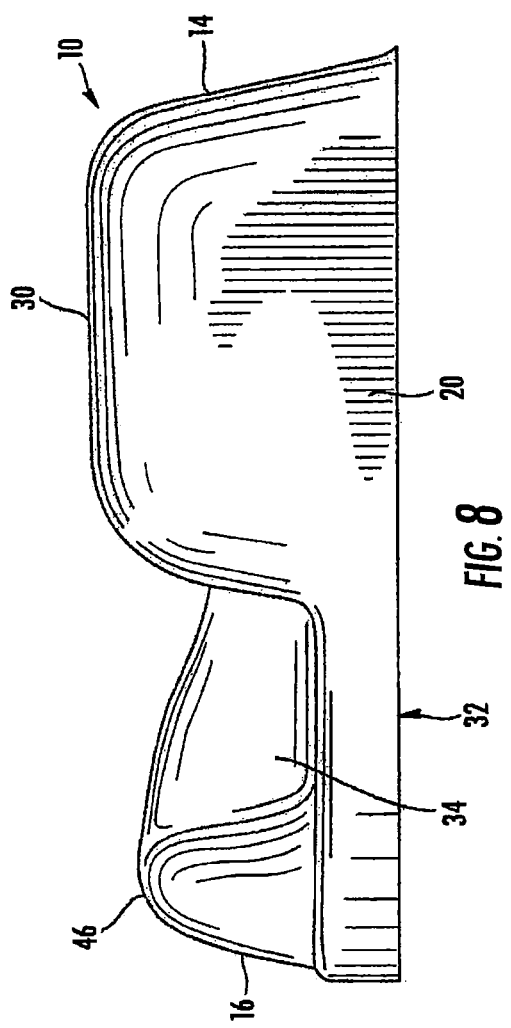
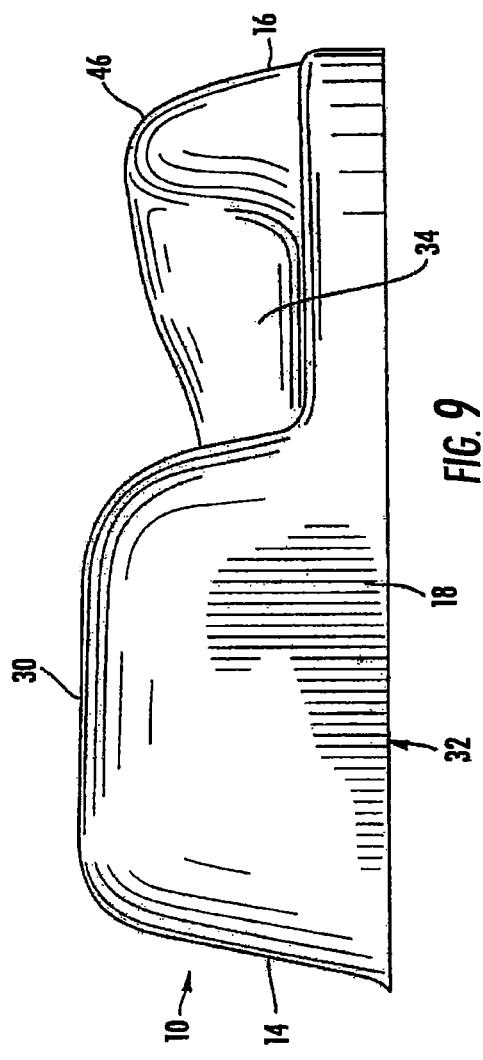

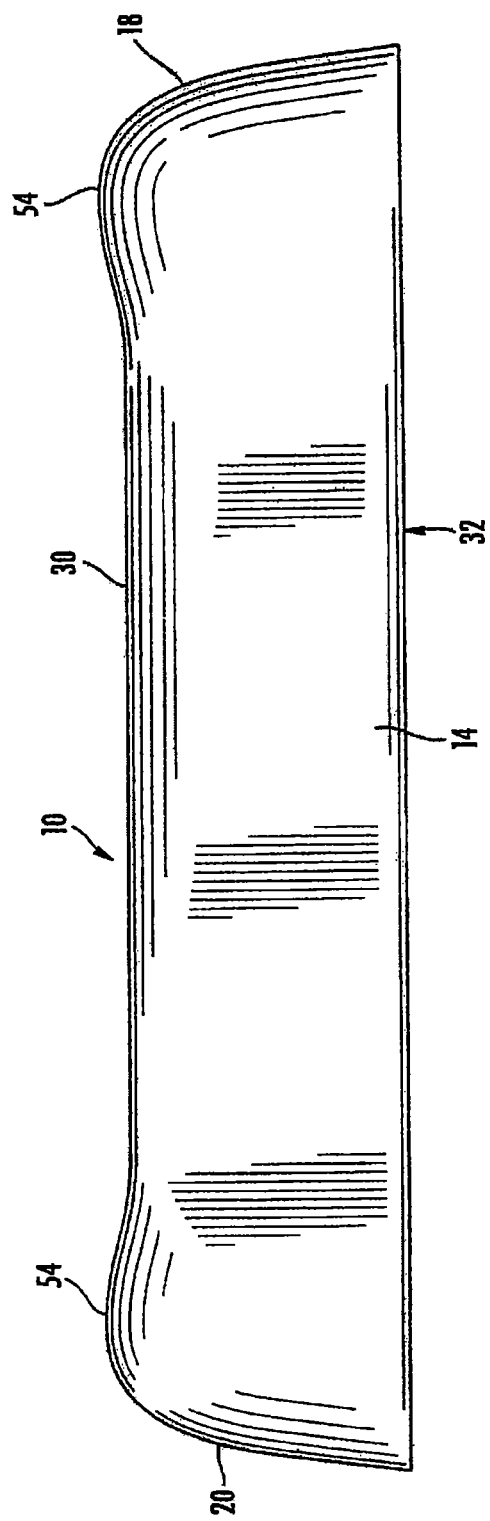

METHODS FOR USING HEAD POSITIONING PILLOWS TO OPTIMIZE RESPIRATORY TITRATION

CROSS-REFERENCES AND RELATED APPLICATIONS

This application is a Continuation of U.S. application Ser. No. 12/698,768, entitled METHODS FOR USING HEAD POSITIONING PILLOWS TO OPTIMIZE RESPIRATORY TITRATION filed on Feb. 2, 2010, the entire contents of which is hereby incorporated by reference in its entirety and priority is claimed under 35 U.S.C. §120.

FIELD OF THE INVENTION

The present invention relates generally to methods for using head positioning pillows to optimize respiratory titration.

BACKGROUND OF THE INVENTION

Respiratory titration is the process of adjusting the output of a respiratory assistive device, such as a respiratory mask attached to a positive airway pressure device to match the patient's needs. Users of respiratory masks often have difficulty resting or sleeping because pressure on the mask exerted by a pillow while side sleeping can impede the performance and comfort of the mask, cause the mask seal to separate from the face and result in air leakage (which can cause irritation from the eyes drying out), and/or cause the mask to press uncomfortably against the user's face. Users of respiratory masks often try to compensate for leaks and positional problems by tightening the mask against the face more than otherwise required, causing further discomfort. The ultimate effect of these problems is sleep interruption or non-compliance by the user (i.e., the user stops using the mask).

In addition, it has also been discovered that titration processes performed in a clinic setting are not effective in the home, which reduces the effectiveness of the respiratory device. The largest variable is the pillow used by the patient. Pillows supporting the head and neck can have a direct impact on the alignment of the patient's airway. Most pillows come in many different constructions and sizes, each of which will change the positioning of the head and neck relative to the upper body and can adversely impact the alignment of the airways and subsequent efficiency of air flow through the trachea, mouth, and throat.

Further, a variety of positioning variables found in the home make it difficult for users of respiratory masks to maintain the salutary effects of a respiratory titration performed in the clinic setting. Accordingly, there remains a need for a device and method to be used in a clinic setting that may then be used at home.

BRIEF SUMMARY OF THE DISCLOSURE

Presented herein are various methods for using head positioning pillows to optimize respiratory titration. More specifically, the method comprises a first step of determining an optimal relative angle between the patient's mouth and throat at which the patient's airway is optimally opened. The method also comprises a second step of adjusting a head positioning pillow relative to the patient's head and neck to modify, transform and optimize the configuration of the pillow to thereby achieve a pillow position that achieves the optimal relative angle.

BRIEF DESCRIPTION OF THE SEVERAL VIEWS OF THE DRAWING(S)

Reference will now be made to the accompanying drawings, which are not necessarily drawn to scale, and wherein:

FIG. 8 is a right side view illustrating the pillow of FIG. 5;

FIG. 9 is a left side view illustrating the pillow of FIG. 5;

FIG. 10 is a rear elevational view illustrating the pillow of FIG. 5;

DETAILED DESCRIPTION OF THE DRAWINGS

Embodiments of the present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form, and vice versa. Also, as used herein, the term "a" shall mean "one or more," even though the phrase "one or more" is also used herein. Like numbers refer to like elements throughout.

In general terms, described herein are various methods for using head positioning pillows to modify and transform the pillow's configuration to optimize respiratory titration. These head positioning pillows are for use with assisted breathing or respiratory masks, such as continuous positive airway pressure ("CPAP") masks, auto adjusting positive airway pressure ("APAP") masks, dual positive airway pressure ("BiPAP") masks, and demand positive airway pressure ("DPAP") masks, and other mask types for oxygen, etc., to facilitate resting and sleep. Respiratory titration, as described herein, is the process of adjusting the output of these and other respiratory assistive devices, such as a head positioning pillow, in order to address individual patient's needs.

Figure 1:
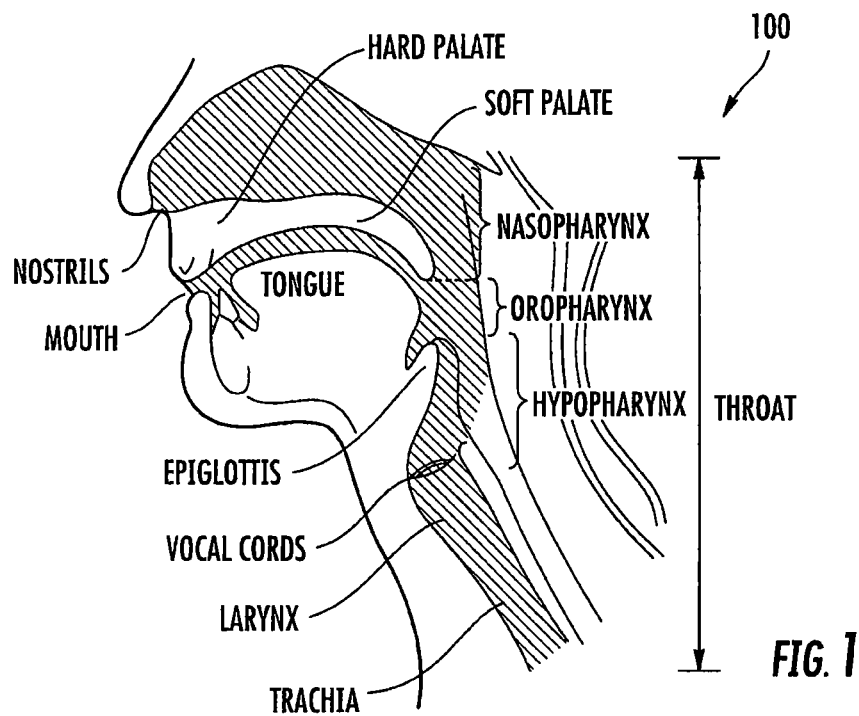
FIG. 1 is a side view of a patient's open airway where the patient's head and neck are positioned in a generally upright position.

FIG. 1 provides an exemplary diagram 100 of a patient's airway and some of its features, including the patient's mouth, nostrils, hard palate, soft palate, and a portion of the patient's throat, which includes a nasopharnyx, oropharnyx, hypopharnyx, epiglottis, vocal cords, larynx, and trachea. Diagram 100 illustrates how these features are positioned relative to each other when the patient's head and neck are positioned in a generally upright position. More specifically, diagram 100 shows that the patient's airway is generally opened, as indicated by the continuous flow of gray shade extending from the nostrils and mouth down through the throat to the trachea.

Figure 2:
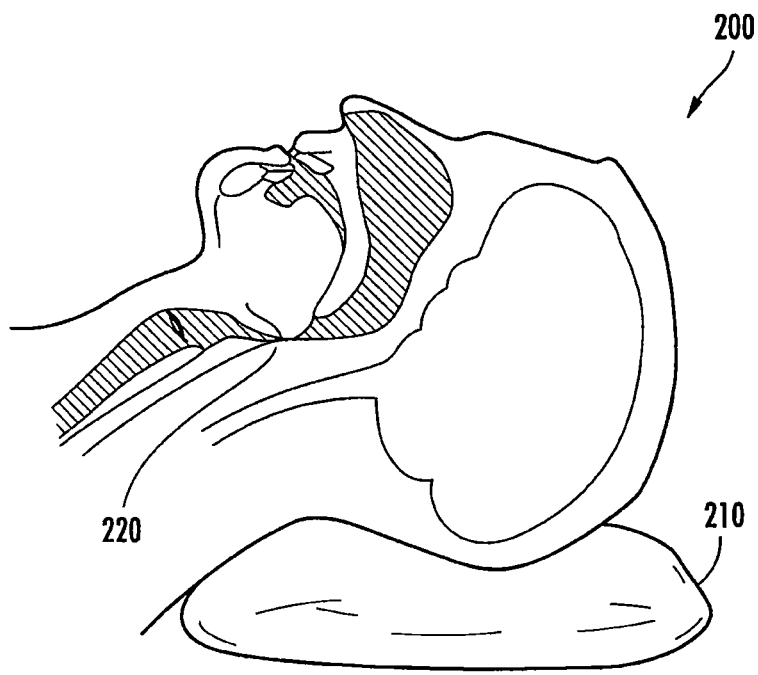
FIG. 2 is a side view of a patient's closed airway where the patient's head and neck are lying in a generally horizontal position.

FIG. 2 provides an exemplary diagram 200 of a patient's closed airway where the patient's head and neck are lying in a generally horizontal position on a regular pillow 210. As shown, the patient's airway is generally closed at position 220, which restricts the patient's ability to breathe. The methods and pillows described herein help patients overcome this problem.

Figure 3:
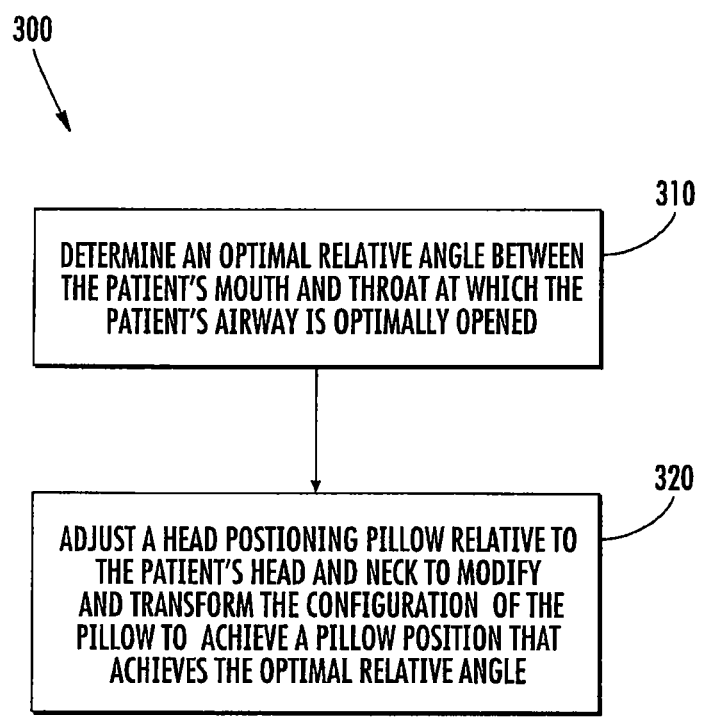
FIG. 3 is a general process flow, according to one embodiment of the present invention.
Figure 4A:
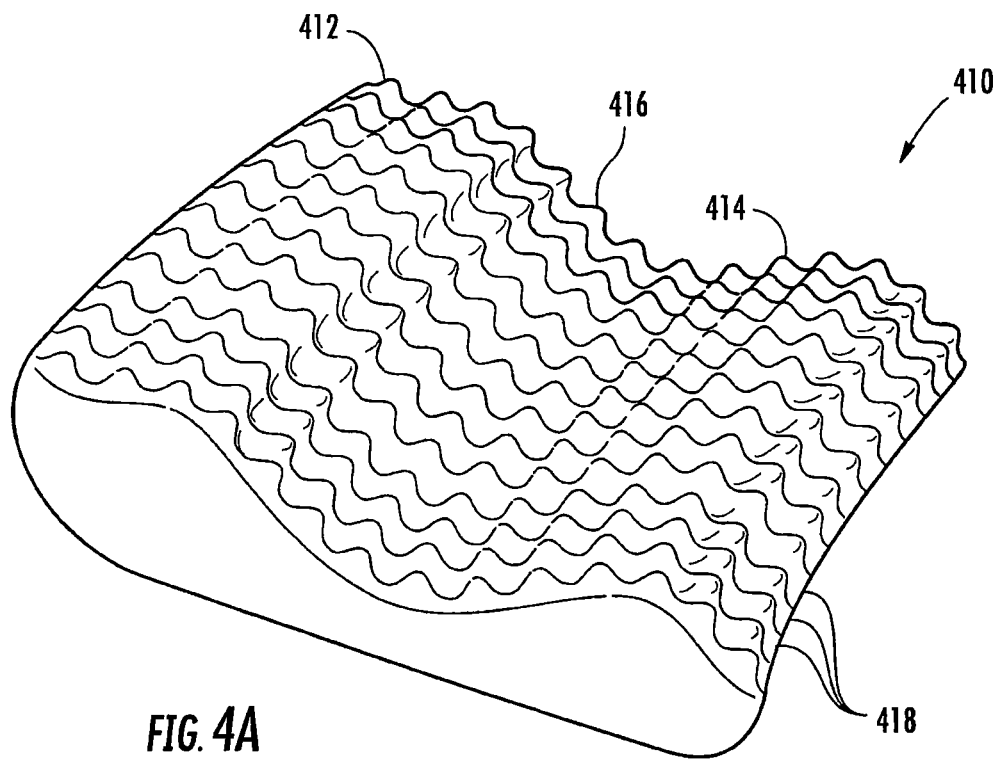
FIG. 4A is a top plan view of one embodiment of a head positioning pillow.
Figure 4B:
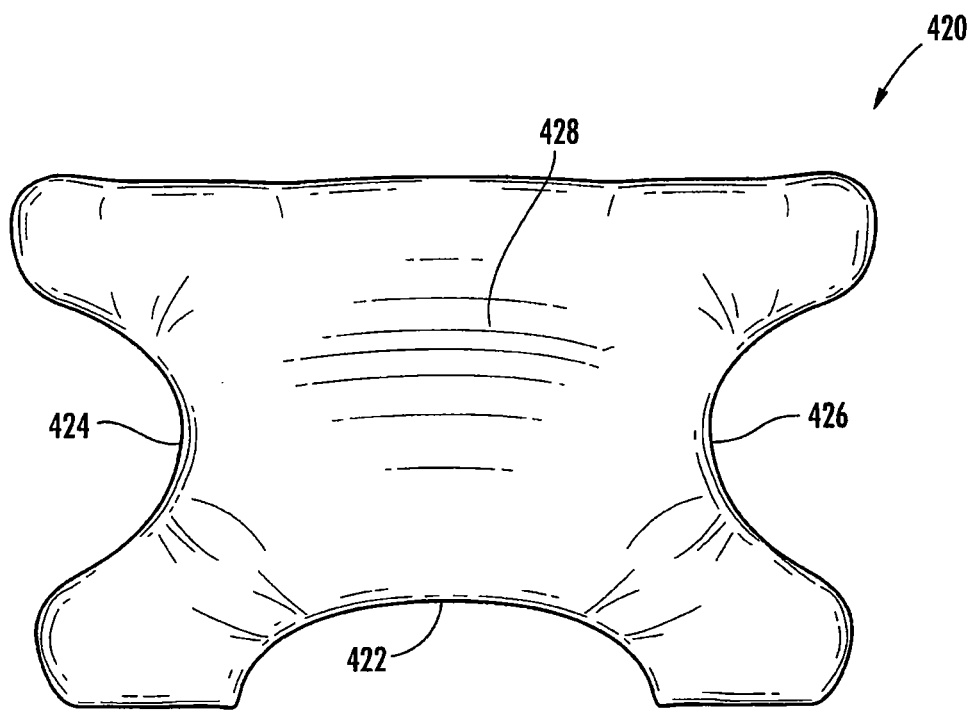
FIG. 4B is a top plan view of one embodiment of a head positioning pillow.
Figure 4C:
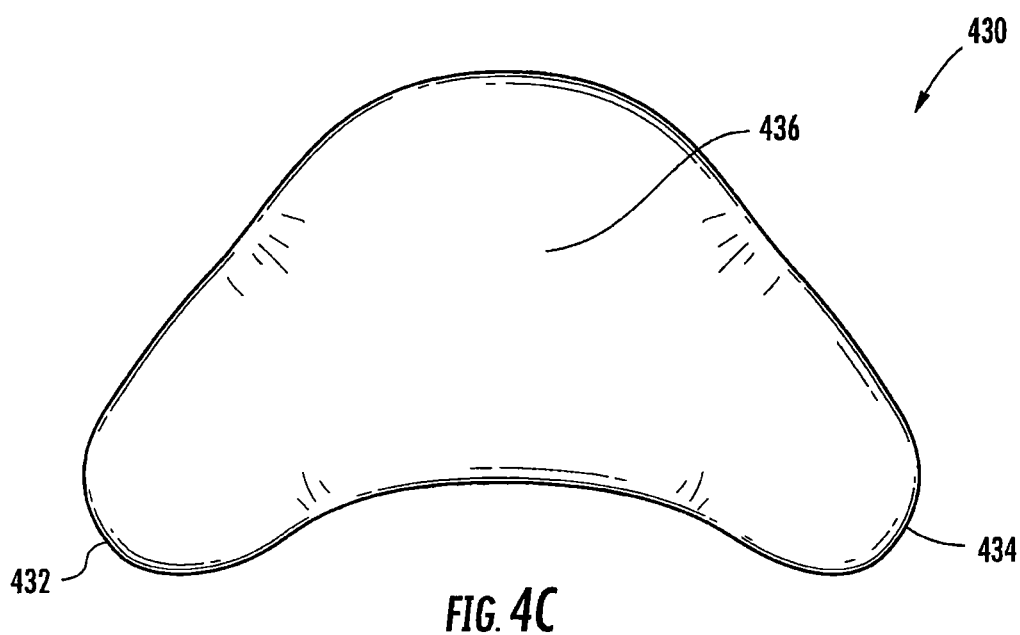
FIG. 4C is a top plan view of one embodiment of a head positioning pillow.
Figure 4D:
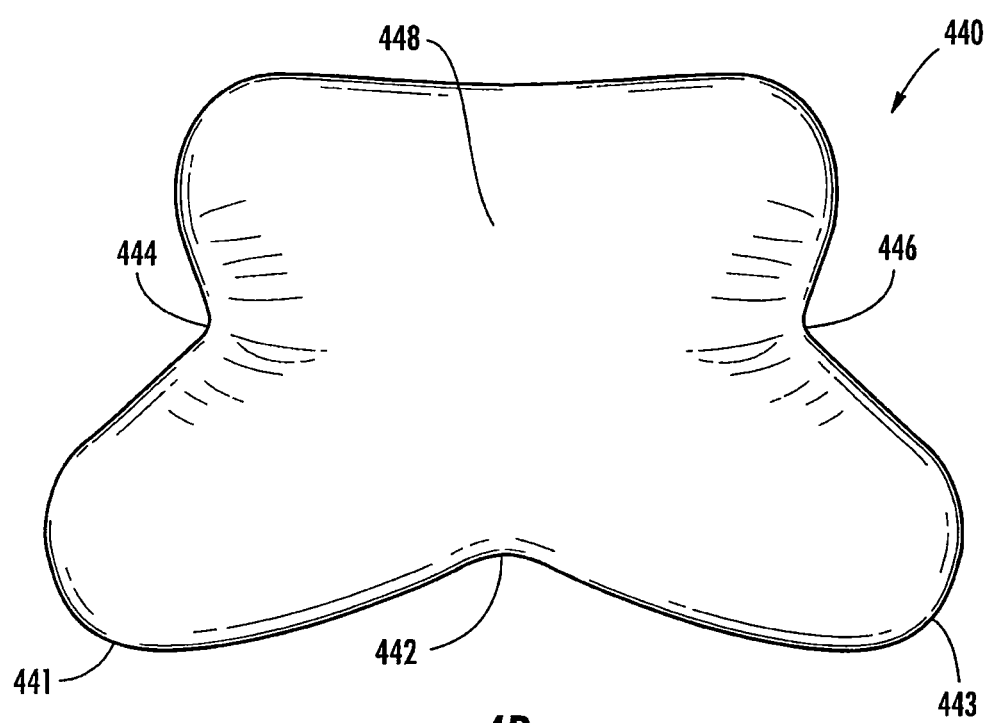
FIG. 4D is a top plan view of one embodiment of a head positioning pillow.

Referring now to a method for using a head positioning pillow to optimize respiratory titration, FIG. 3 provides an exemplary flow diagram illustrating a general process flow 300. As represented by block 310, the first step is to determine an optimal relative angle between the patient's mouth and throat at which the patient's airway is optimally opened. The next step is to adjust a head positioning pillow to modify and transform the configuration of the pillow relative to the patient's head and neck to achieve a pillow position and configuration that achieves the optimal relative angle, as illustrated by block 320.

The order of the steps described in blocks 310 and 320, in FIG. 3 may vary. For example, in one embodiment, the step described in block 320 may occur before, after, or substantially simultaneous with the step described in block 310.

In other embodiments of the present invention, general process flow 300 may include other steps. One embodiment may divide the step represented by block 320 into two or more separate steps, i.e., a step of adjusting the pillow relative to the patient's neck to modify and transform the configuration of the pillow may be separate from a step of adjusting the pillow relative to the patient's head. Another embodiment may include the steps of measuring the flow of air through the patient's airway and comparing that flow to a target flow rate. A further embodiment may provide for one or more iterative steps, i.e., the step of repeating one or more of the other process steps to, for example, determine via trial and error a relative angle between the patient's mouth and throat at which air flow through the patient's airway is maximized.

In many of the embodiments of general process flow 300, the head positioning pillow is adjustable. Adjustable head positioning pillows directly impact the alignment of the patient's airway and affect the flow of air through the patient's trachea, throat, and mouth. Accordingly, they are particularly helpful in "tuning" the patient's airway alignment and efficiency during any kind of respiratory titration process, including methods involving CPAP, BiPAP, DPAP, and APAP titration. These features are also helpful when used in connection with surgical procedures where the patient uses assisted respiration.

In one embodiment, the pillow is height adjustable, such that a rear side, a front side, a first lateral side, and/or a second lateral side of the pillow can adjust in height to better align the patient's head and neck. In other embodiments, other features of the pillow, including a central indentation and/or a raised section, are adjustable to help raise or lower the patient's head and neck.

In another embodiment of the present invention, the pillow is adjustable by increasing or reducing the support of the patient's neck. For example, a section of the pillow that contacts the patient's neck and/or head can include a bladder in which air or fluid can be added or released to adjust the elevation and amount of support provided. In other embodiments, an indentation and/or a raised area of the pillow may adjust in other ways to properly align and support the patient's neck.

In still another embodiment of the present invention, the pillow may be adjustable by changing the rotation of the patient's head and/or neck position. Other embodiments may include a pillow that adjusts to change the incline angle of the patient's head and/or neck position.

The adjustable pillows described herein are important only if used correctly. More specifically, it is important that patients are able to utilize the optimized respiratory titration process and reconfigured pillow that is initially performed in a clinic setting or in the home setting, when they are away from that setting. By increasing the user's compliance, fewer inconsistencies are introduced into the patient's daily respiratory process, which creates less of a need to "overcorrect" certain settings on the respiratory device to deliver the proper air flow. For example, many patients will correct for mask leaks by increasing the pressure setting on the respiratory device. By providing a configured pillow optimized for the patient, a patient does not need to readjust the respiratory device, and this helps to reduce unintended side effects.

Referring now to FIG. 4, four embodiments of a head positioning pillow are illustrated. Pillow 410 includes raised back section 412, raised front section 414, central recess section 416, and a plurality of raised contact points 418. Pillow 420 includes front receding edge 422, side receding edges 424 and 426, and central raised section 428. Pillow 430 includes side wings 432 and 434, and central raised section 436. Pillow 440 includes front receding edge 442, side receding edges 444 and 446, central raised section 448, and side wings 441 and 443.

Other embodiments of a head positioning pillow 10 are described in FIGS. 5-17. Pillow 10 includes a pliable and resilient body 12, which can be formed of any suitable material, non-exhaustive examples of which include polymer foam, gel, fiber fill inside a casing, and fluid inside a bladder. The configuration of the pillow 10 may vary. In the embodiment illustrated in FIG. 5, the pillow 10 is generally rectangular in shape and includes a rear side 14, a front side 16, a first lateral side 18, and a second lateral side 20. Preferably but not necessarily, the pillow 10 has an axis of symmetry 22 extending between the rear side 14 and front side 16. The pillow 10 has a width W extending between the first lateral side 18 and the second lateral side 20 and a length L extending between the rear side 14 and the front side 16

Figure 6:
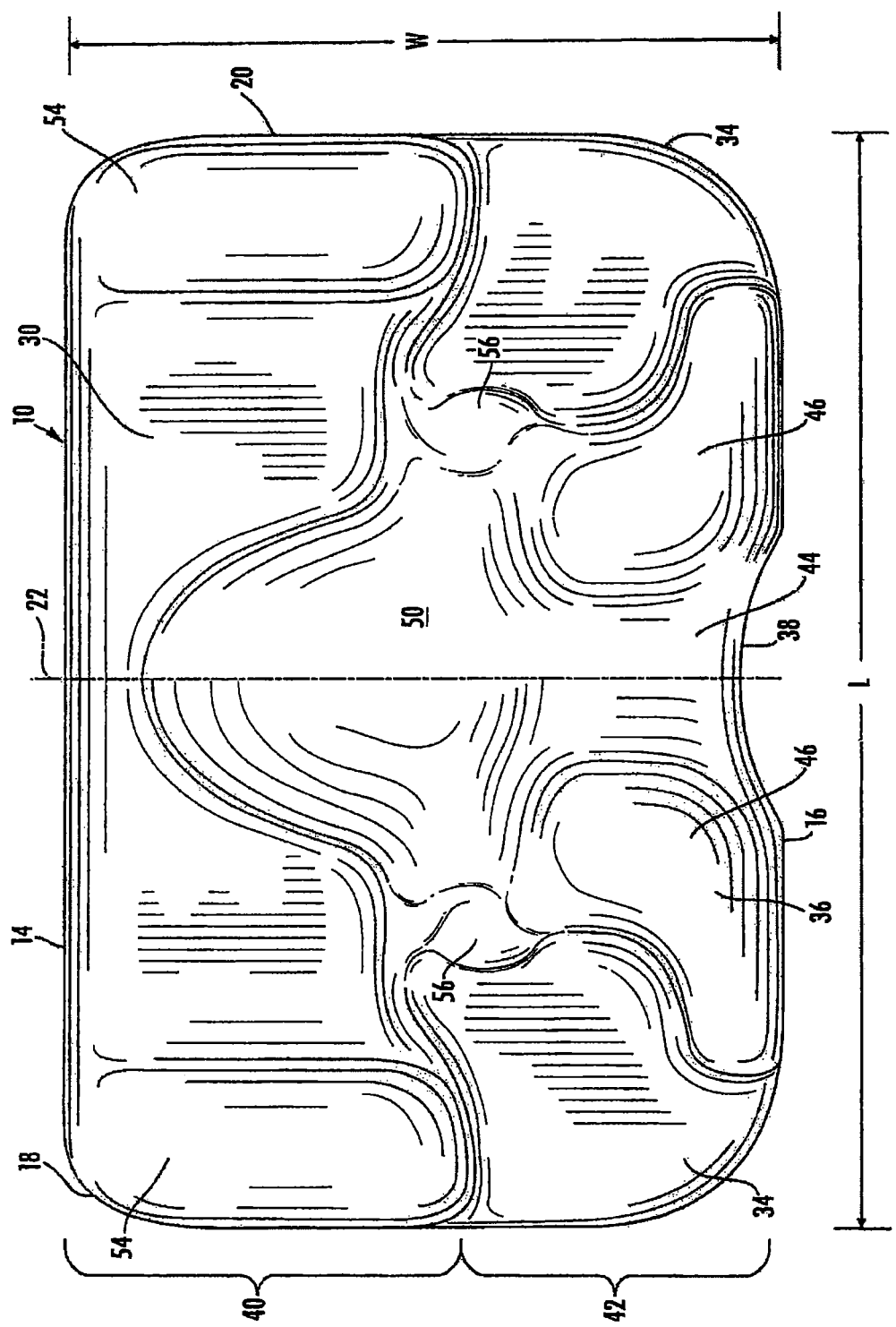
FIG. 6 is a top plan view illustrating the pillow of FIG. 5.
Figure 7:
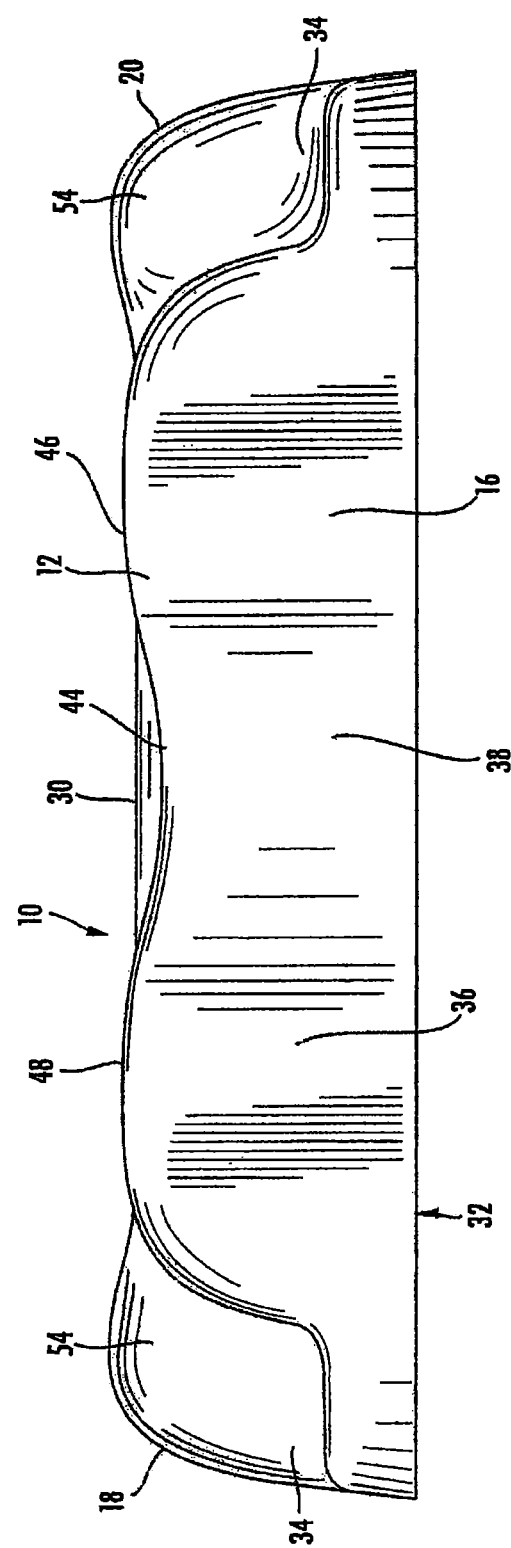
FIG. 7 is a front elevational view illustrating the pillow of FIG. 5.
Figure 11:
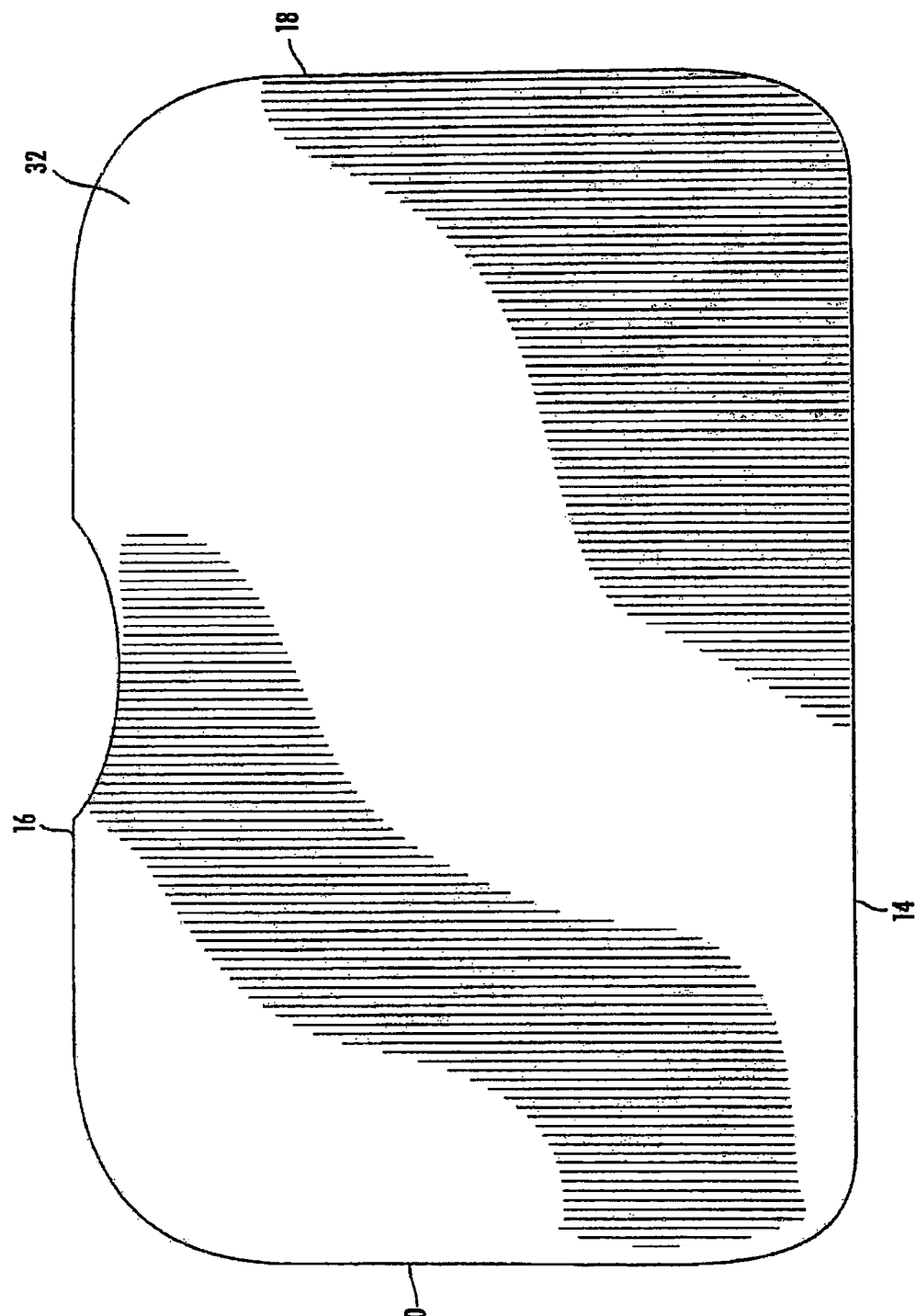
FIG. 11 is a bottom plan view illustrating the pillow of FIG. 5.
Figure 12:
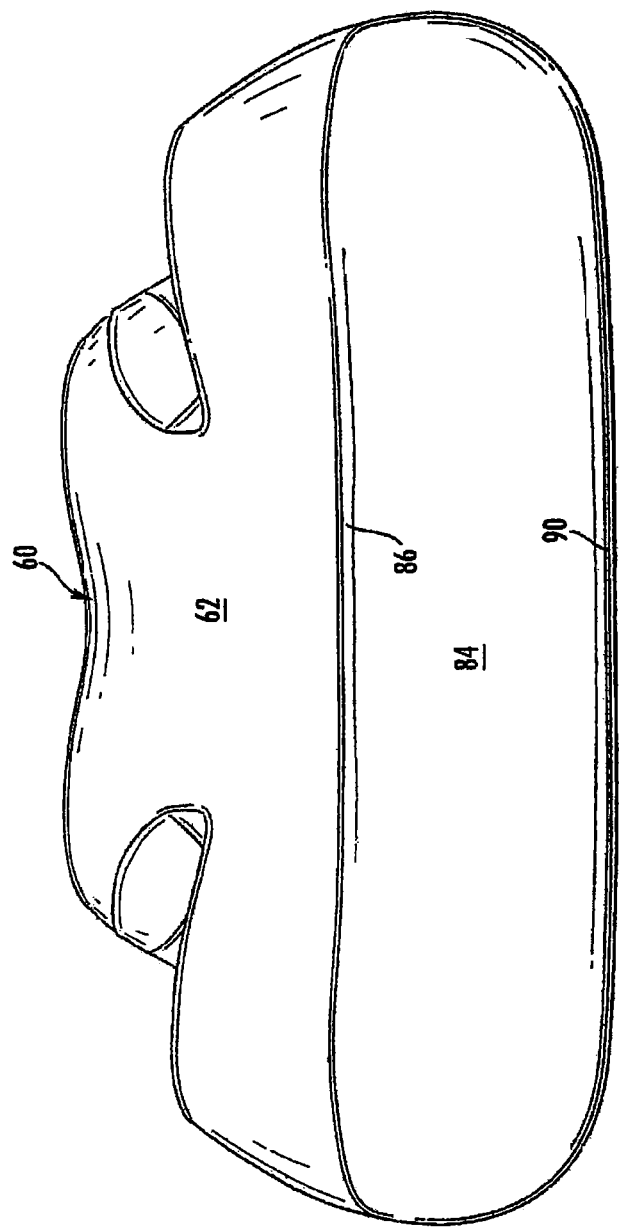
FIG. 12 is a rear view illustrating the cover for the pillow of FIG. 5.

(shown in FIG. 6). The pillow 10 includes a head-supporting upper surface 30 and an opposite bottom surface 32. As illustrated in FIG. 11, the bottom surface is relatively planar. In another embodiment (not shown), the bottom surface 32 may optionally include a plurality of ridges.

The body 12 includes a first portion 40 and a second portion 42 that are preferably formed together as a unitary member. The first portion 40 and second portion 42 of the body 12 are preferably fabricated from the same material, such as foam, fiber fill, gel, etc., that provides good support and resiliency and, optionally, memory properties. The body 12 could also be a form-shaped bladder (not shown) inflated with air or liquid. The invention is not limited to any particular material making up the body 12.

Figure 17:
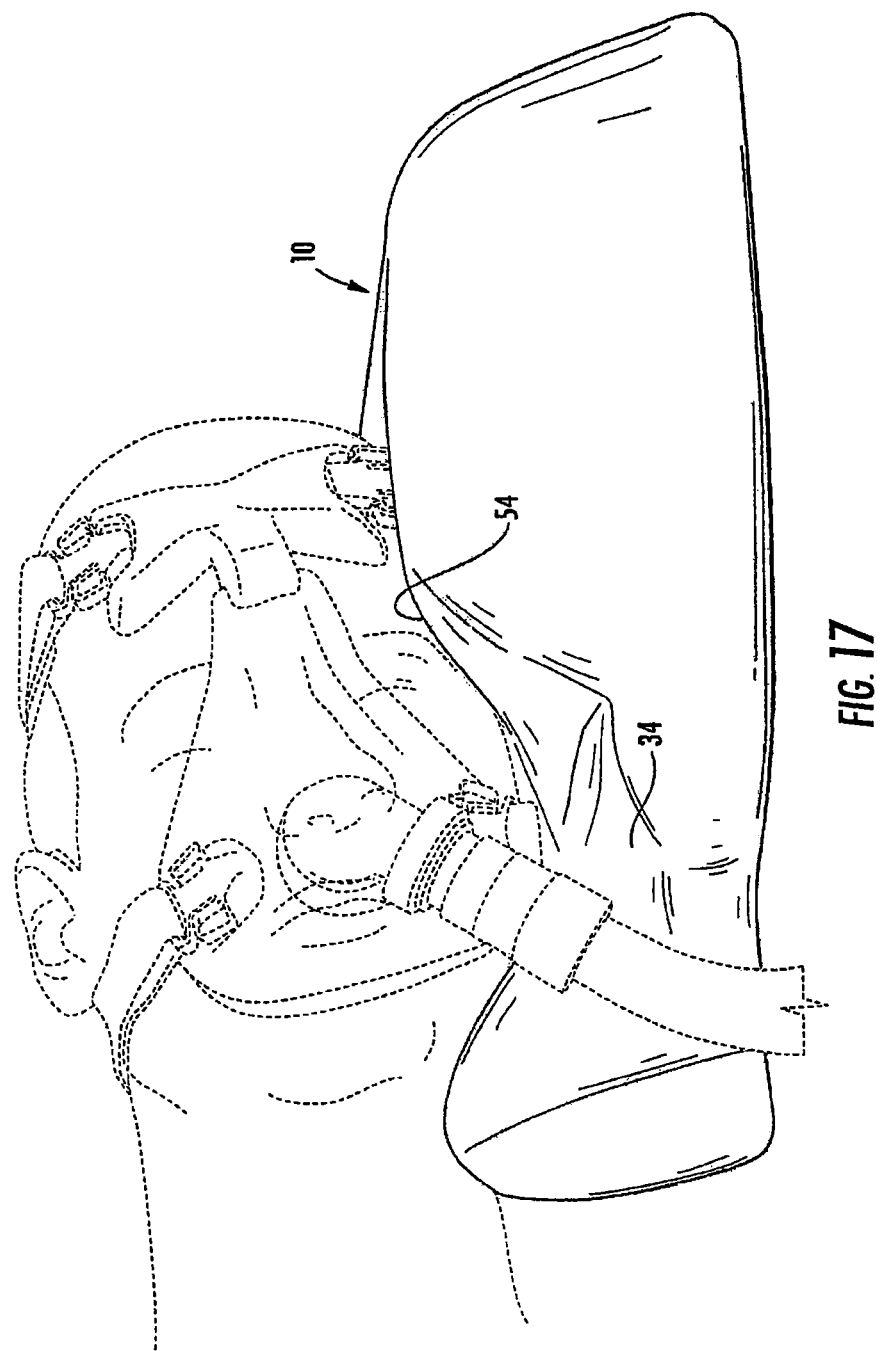
FIG. 17 shows a user wearing a respiratory mask and in a side-lying position with his/her head supported on the pillow of FIG. 5.

According to the embodiment illustrated in FIGS. 5-11, the first portion 40 and second portion 42 of the body 12 are generally rectangular in shape. The upper surface of the second body portion 42 includes a recess 34 adjacent to each of the first lateral side 18 and second lateral side 20 of the body 12 and a raised section 36 therebetween. Advantageously, as illustrated in FIG. 17, the recesses 34 provide pressure relief on the mask when the user of the pillow 10 is resting or sleeping on his/her side, so that the pillow will not exert any substantial degree of pressure on the mask and tubing for the mask. As illustrated in FIG. 6, one or both of the recesses 34 may extend into the first portion of the body 12. The recesses 34 are adjacent to pillow surfaces that comfortably support the user's head in the side-lying position, as further described below.

In one embodiment, as illustrated in FIG. 6, the second portion 42 of the body 12 can include an indentation 38 in the front side 16. This indentation 38 provides a curved area for the user's shoulder to rest for proper position and neck support when in the side-lying position.

Figure 5:
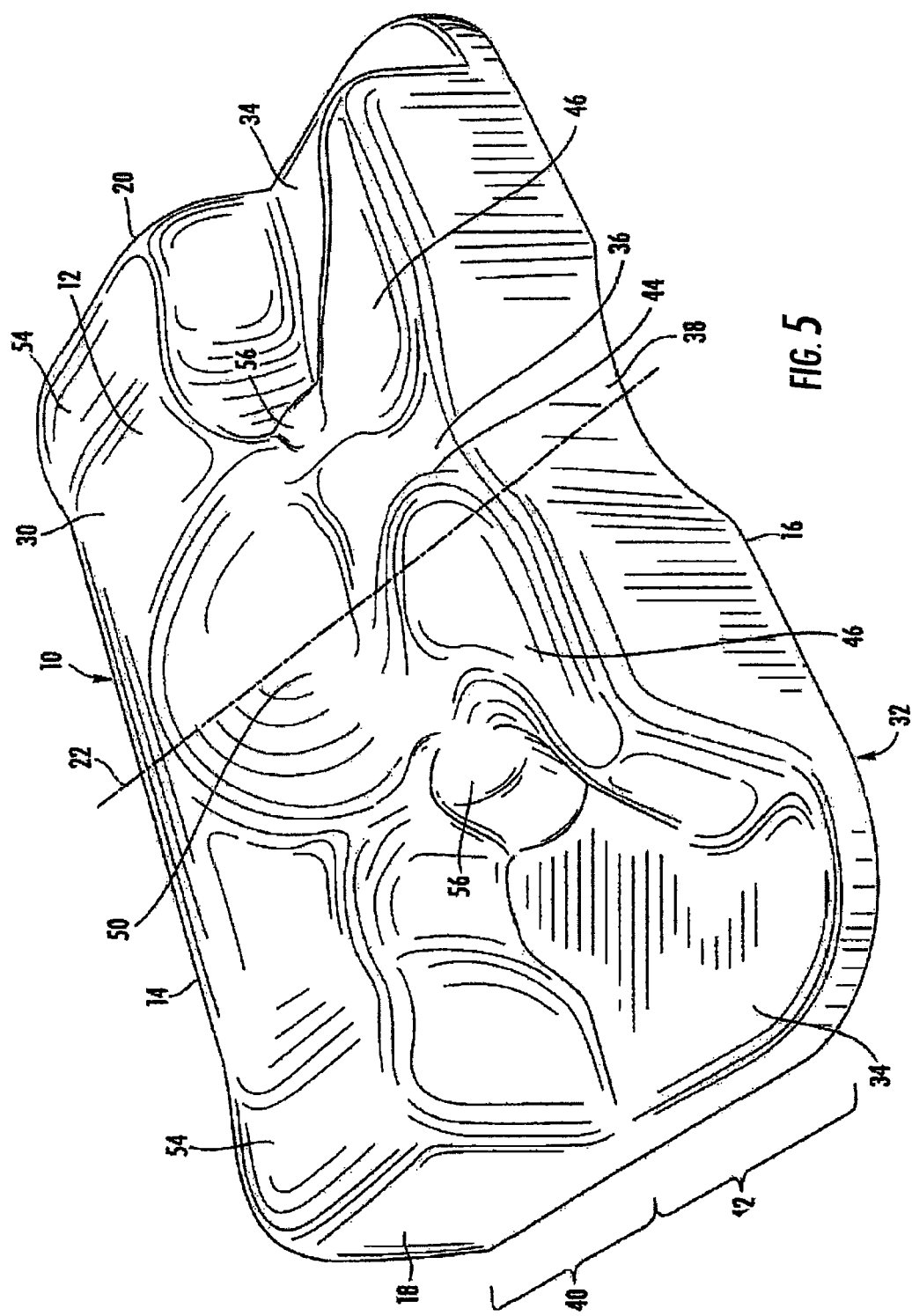
FIG. 5 is a perspective view of a pillow, according to one embodiment of the invention.

The raised section 36 of the second portion 42 of the body 12 provides neck support for both back and side sleeping and resting. In one embodiment (not shown), the raised section 36 can include a bladder in which air or fluid can be added or released to adjust the elevation and amount of support provided. As illustrated in FIG. 5, the upper surface 30 of the raised section 36 may include an indentation 44 with raised areas 46 on each side of the indentation. Advantageously, the indentation 44 receives the user's neck and the raised areas 46 function to retain the user's neck within the indentation while the user is resting or sleeping.

In addition to recesses 34, as illustrated in FIGS. 5 and 6, the upper surface 30 of the body 12 may include a central indentation 50. The edge of the central indentation 50 in the first portion 40 of the body is curved and gently sloping to thereby provide a head support area for the user. As with the indentation 44 and raised areas 46 of the raised section 36, the central indentation 50 receives the user's head and the sloped side walls about the periphery of the central indentation function to retain the user's head within the central indentation while the user is resting or sleeping.

Referring to FIG. 10, the first portion 40 of the body 12 may include raised areas 54 adjacent to each of the first lateral side 18 and second lateral side 20. As illustrated in FIG. 17, the raised areas 54 provide support to the user's forehead when resting or sleeping in the side position to keep the user's head from rotating downward.

Referring to FIGS. 5 and 6, on either side of and adjacent to the indentation 44 and the central indentation 50, secondary recessed areas 56 may be provided. These secondary recessed areas 56 are for receiving either of the user's ears when in either of the left and right side-lying positions, to help relieve excess pressure on the ears and thereby improve overall comfort of the user.

In other embodiments (not shown), the pillow 10 can include other structure to accommodate or secure a hose for a respiratory mask. In one embodiment, the structure may include a routing channel or aperture formed into the pillow to reduce interference with the hose.

Typical materials of which the body 12 can be made (such as polymer foam, gel, fluid-filled bladders, etc.) may not be very comfortable if the skin is in direct contact with them, because they may not "breathe" very well. Accordingly, in preferred embodiments of the invention, a cover is provided for the pillow in order to enhance the comfort of the pillow. Referring to FIGS. 12-15, a fitted cover 60 for the pillow 10 is illustrated. It is important for the cover to substantially conform to the contours of the pillow, and in particular to the mask-receiving recesses 34, in order for the recesses to function properly to relieve pressure on the mask.

Figure 13:
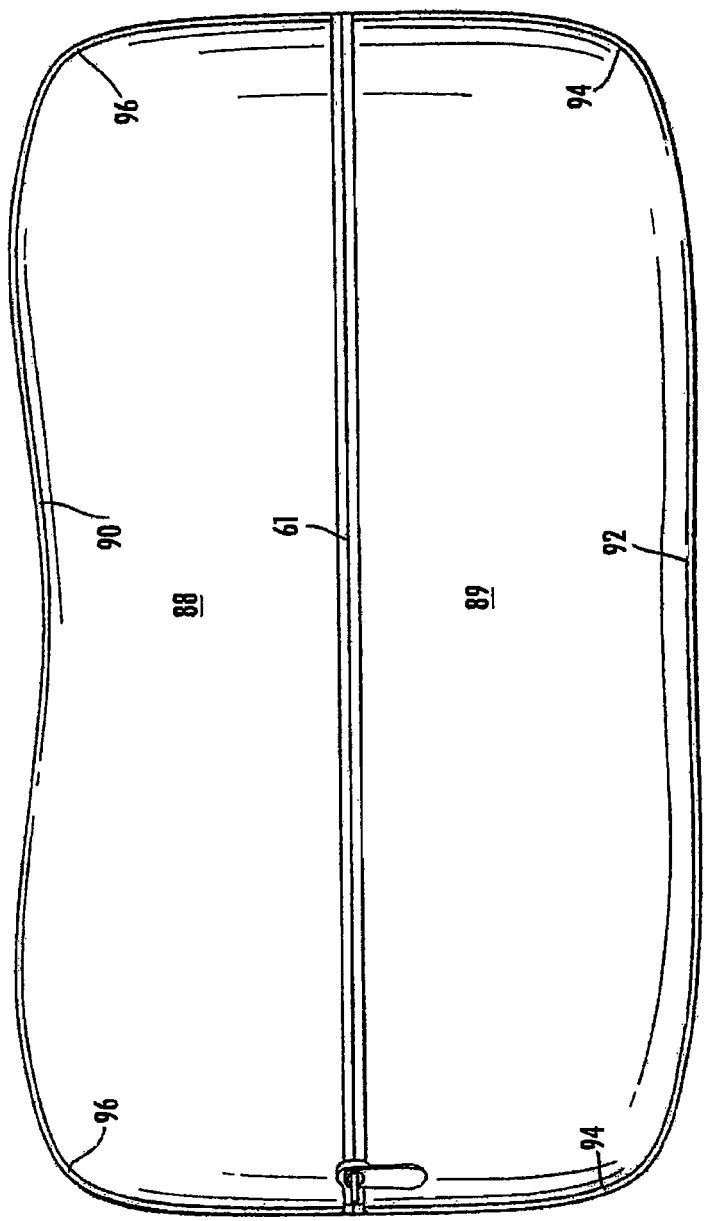
FIG. 13 is a bottom plan view illustrating the cover of FIG. 12.
Figure 14:
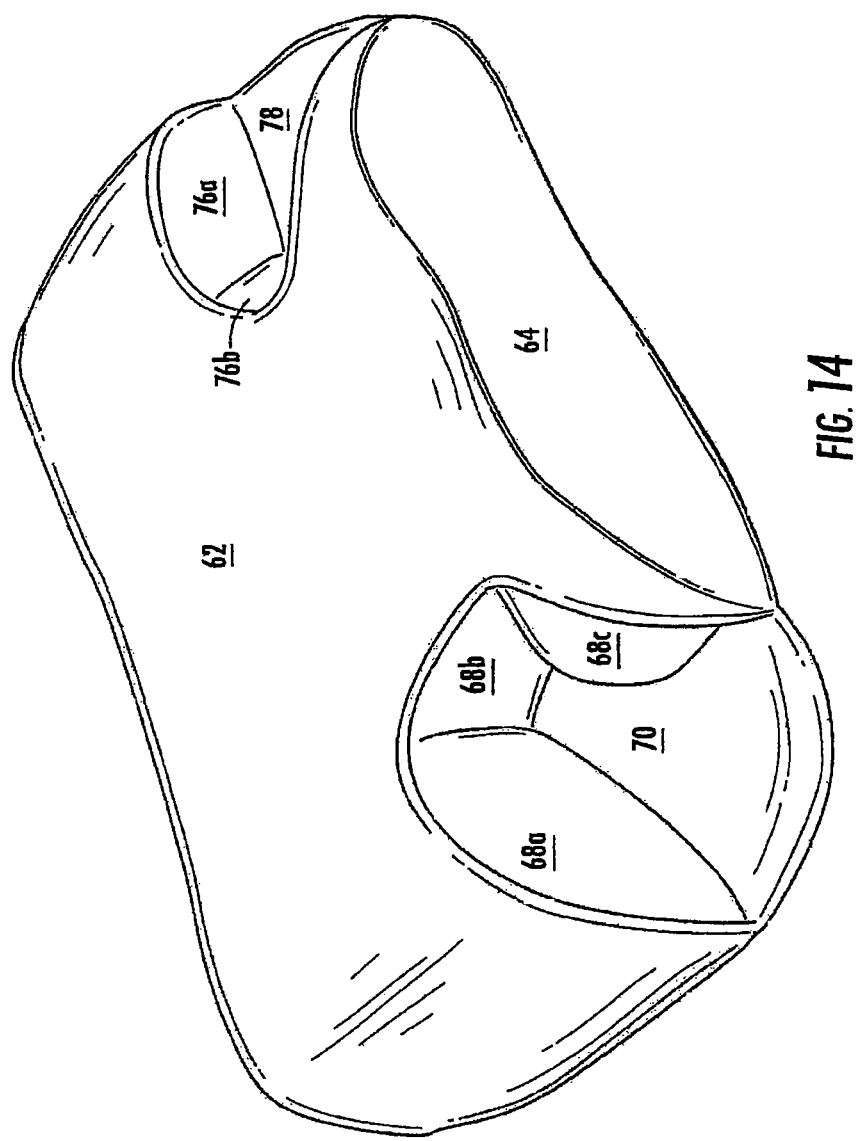
FIG. 14 is a perspective view illustrating the cover of FIG. 12.
Figure 15:
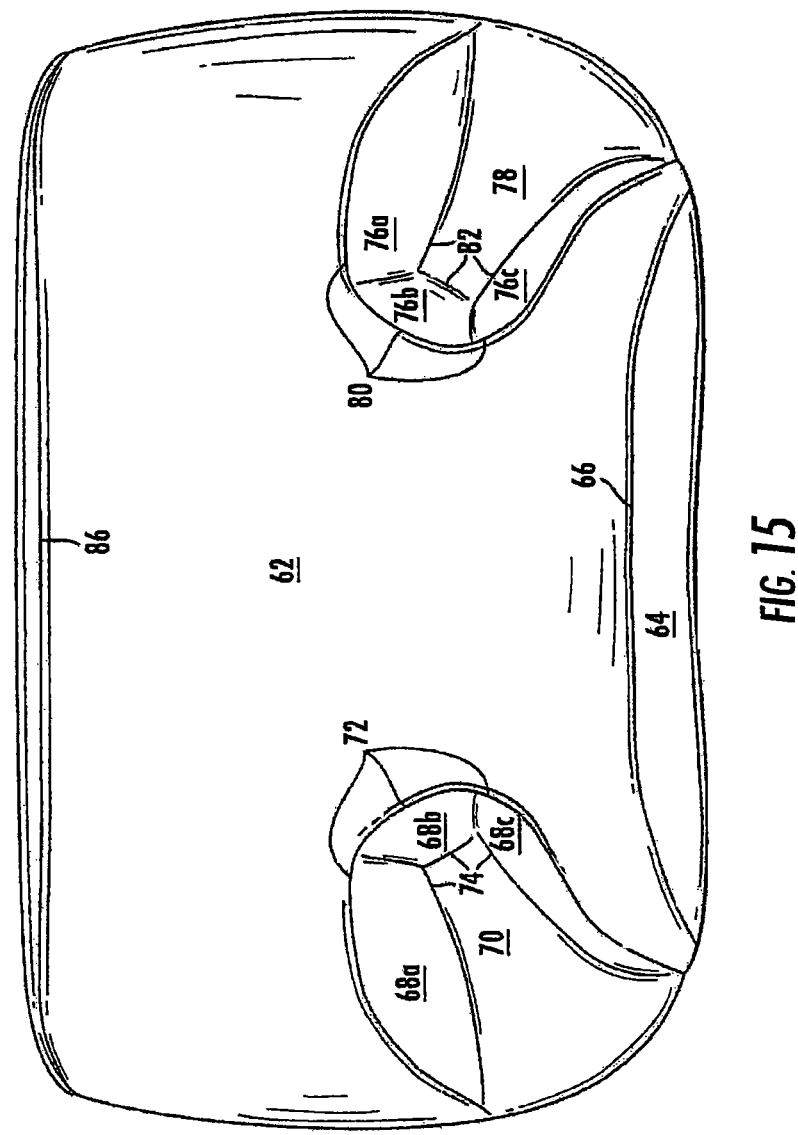
FIG. 15 is a top plan view illustrating the cover of FIG. 12.

As shown in FIG. 13, the fitted cover preferably includes an opening 61 on the bottom side of the cover corresponding to the bottom surface of the pillow, so that the pillow may be inserted into and removed from the cover to enable cleaning of the cover. As shown, a zipper is provided for closing the opening 61. As illustrated in FIGS. 12-15 and as discussed above, the cover is preferably fitted so that the cover substantially follows the contours and configurations of the pillow, and particularly those depressions, recesses, cavities, apertures, and/or raised portions that are structured to accommodate the mask or tubing for the mask. The cover 60 may also include structure to accommodate or secure a hose for the mask. In one embodiment (not shown), the structure of the cover may include one or more tethers to keep the hose from sliding or being positioned unfavorably. The cover can be sewn to fit the pillow. The cover may be made of a material that can be formed to fit the contours of the pillow by pressure, heat, or other means. Alternatively, instead of a separately made cover that is removable, the cover may comprise a material permanently applied to the surface of the pillow by any of various techniques, such as painting, dipping, or spraying. For example, flocking may be sprayed onto the pillow and adhered thereto by a suitable adhesive material.

In a preferred embodiment as shown in FIGS. 12-15, the cover 60 is a fitted cover made from pieces of fabric sewn together. More particularly, a first fabric piece 62 is sized and shaped to cover the majority of the upper surface of the pillow except for the recesses that receive the mask. The first fabric piece also drapes down over the opposite lateral sides of the pillow (except in the regions of the recesses). A second fabric piece 64 is sized and shaped to cover the front side and is sewn to the first fabric piece along a seam 66. Third, fourth, and fifth fabric pieces 68a, 68b, 68c are sized and shaped to cover the steeply sloped walls of the left-hand recess of the pillow, and a sixth fabric piece 70 is sized and shaped to cover the bottom wall of that recess. The fabric pieces 68a-c are sewn to the first fabric piece 62 along seams 72. The sixth fabric piece 70 is sewn to the fabric pieces 68a-c along seams 74.

Seventh, eighth, and ninth fabric pieces 76a, 76b, 76c are sized and shaped to cover the steeply sloped walls of the right-hand recess of the pillow, and a tenth fabric piece 78 is sized and shaped to cover the bottom wall of that recess. The fabric pieces 76a-c are sewn to the first fabric piece 62 along seams 80. The fabric pieces 76a-c are sewn to the tenth fabric piece 78 along seams 82. An eleventh fabric piece 84 (FIG. 12) is sized and shaped to cover the rear side of the pillow and is sewn to the first fabric piece 62 along a seam 86. Finally, twelfth and thirteenth fabric pieces 88, 89 (FIG. 13) are sized and shaped to cover the bottom surface of the pillow and are sewn to the eleventh fabric piece 84 along a seam 90, to the second fabric piece 64 along a seam 92, to the opposite edges of the first fabric piece 62 along seams 94, and to the sixth and tenth fabric pieces 70, 78 along seams 96.

Various types of fabric (woven, knitted, non-woven, etc.) made from various fiber types (natural, synthetic, natural/synthetic blends, etc.) can be used to make the sewn cover 60. In one embodiment, quilted woven fabric is employed for part of the cover and knitted fabric is employed for the rest. More particularly, in one embodiment, fabric pieces 62, 84, 88, and 89 are knitted fabric, with velour being particularly preferred. Fabric pieces 64, 68*a-c*, 70, 76*a-c*, and 78 are quilted woven fabric.

Figure 16:
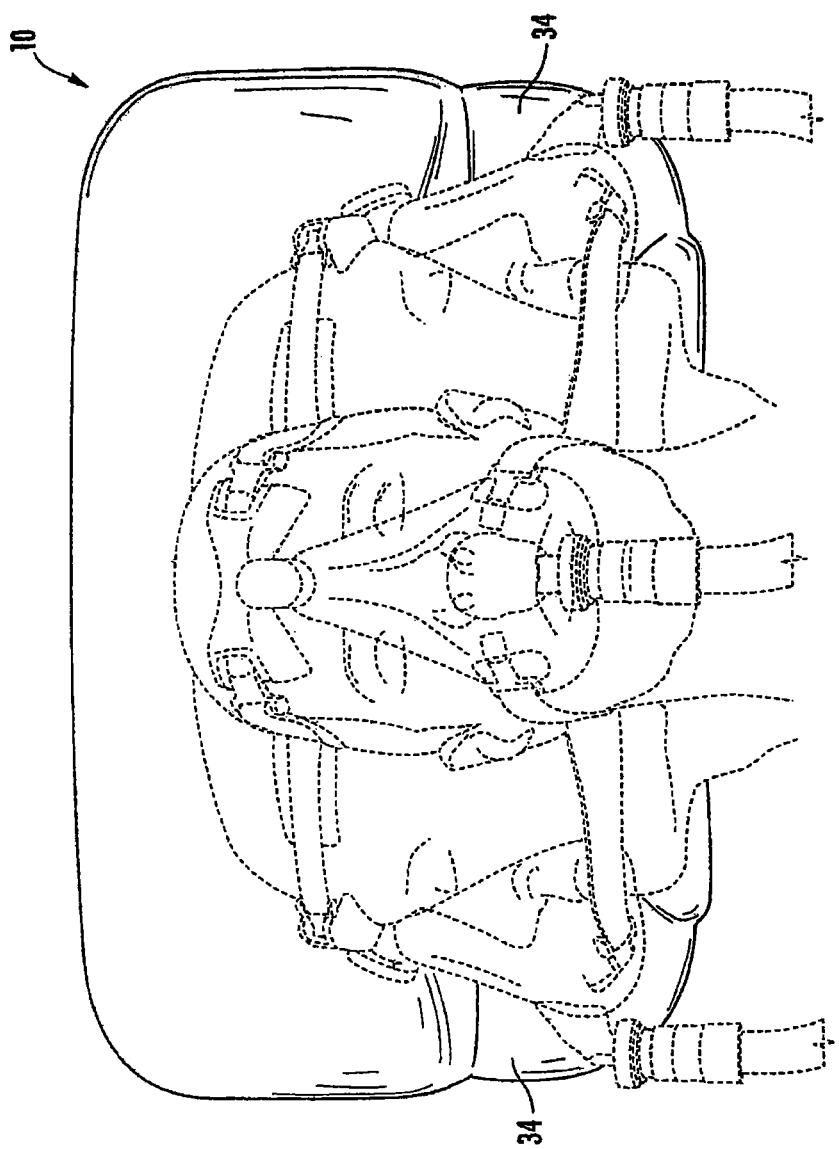
FIG. 16 shows a user wearing a respiratory mask and in a back-lying position with his/her head supported on the pillow of FIG. 5.

Referring to FIGS. 16 and 17, the pillow 10 is shown in use in the back- and side-lying positions. The pillow of the present invention may also be used in the stomach sleeping and resting positions. Advantageously, the cover of the pillow substantially follows the contours of the pillow and provides the user with contact-free use of a respiratory mask and the ability to easily sanitize the pillow after use. According to one embodiment, the pillow is used by positioning a cover on the pillow such that the cover substantially follows the contours and configurations of the pillow. A respiratory mask is positioned on the user's head. The user is positioned so that the user's shoulder is received in the lateral indentation 38 formed in the front side 16 of the second portion 42 of the pillow. The user's neck is positioned within the indentation 44 formed in the raised section 36 of the second portion 42 of the pillow. The user's head is positioned within the central indentation 50 formed in the first portion 40 of the pillow. In one embodiment, the positioning of the user's head comprises positioning the user's head so that it is facing away from the pillow. In another embodiment, the positioning of the user's head comprises positioning the user's head so that the side of the user's head is in contact with the cover of the pillow. In one embodiment, the method includes positioning the mask or hose for the mask in one of the recesses 34 formed in the second portion 42 of the pillow so that the pillow does not exert substantial pressure on the mask or hose.

In sum, the various embodiments of the head positioning pillow of the present invention may have depressions, recesses, cavities, apertures, and/or raised portions to accommodate various respiratory masks, such as those used for nighttime respiratory therapy. The depressions, recesses, cavities, apertures, and/or raised portions relieve pressure against the mask and the hoses or tubing supplying the mask when side sleeping or stomach sleeping. Since pressure against the mask can impede the performance and comfort of the mask, cause the mask seal to separate from the face and result in air leakage (which can cause irritation from the eyes drying out), and/or cause the mask to press uncomfortably against the user's face, the embodiments of the pillows of the present invention and method of using the same eliminate many of the impediments to the user resting or sleeping while using a respiratory mask. Advantageously, the pillow and cover of the present invention allow the user to move and sleep in multiple positions—left side, right side, back, and stomach—while minimizing the pressure that is exerted on the respiratory mask.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for using head positioning pillows to optimize respiratory titration, the method comprising:
   determining an optimal relative angle between the patient's mouth and throat at which the patient's airway is optimally opened; and
   adjusting a head positioning pillow relative to the patient's head and neck, wherein the head positioning pillow comprises at least one of a depression, recess, cavity, aperture and raised portion structured to accommodate a respiratory mask positioned on the patient's head, to thereby modify and transform the configuration of the pillow to achieve a pillow position that achieves the optimal relative angle.

2. A method according to claim 1 further comprising adjusting the head positioning pillow relative to the patient's head and the respiratory mask secured thereon in order to relieve pressure against the mask and the hoses or tubing supplying the mask.

3. A method according to claim 1 wherein the pillow comprises a cover.

4. A method according to claim 3 wherein at least a portion of the cover comprises a knitted fabric.

5. A method according to claim 3 wherein at least a portion of the cover comprises a quilted woven fabric.

6. A method according to claim 3 wherein the cover of the pillow substantially follows the contours and configurations of the pillow.

7. A method according to claim 1 wherein the respiratory mask comprises a continuous positive airway pressure mask, auto adjusting positive airway pressure mask, dual positive airway pressure mask or demand positive airway pressure mask.

8. A method according to claim 1 wherein said adjustment step comprises adjusting the height of at least one of the rear side, front side, first lateral side or second lateral side of the pillow.

9. A method according to claim 1 wherein said adjustment step comprises increasing or reducing the support of the patient's neck.

10. A method according to claim 1 wherein said adjustment step comprises adjusting the pillow to change at least one of the incline angle of the patient's head or neck.

11. A method according to claim 1 further comprising adjusting the rotation of at least one of the patient's head or neck.

12. A method according to claim 1 wherein the pillow comprises a fluid-filled bladder.

* * * * *

UNITED STATES PATENT AND TRADEMARK OFFICE
CERTIFICATE OF CORRECTION

PATENT NO. : 9,623,202 B2
APPLICATION NO. : 14/552243
DATED : April 18, 2017
INVENTOR(S) : Edmund Scott Davis and Antonio Arcieri It is certified that error appears in the above-identified patent and that said Letters Patent is hereby corrected as shown below:

On the Title Page

Priority to provisional patent application No. 61/138,040, filed on December 16, 2008, should be listed Signed and Sealed this
First Day of May, 2018

Andrei Iancu
*Director of the United States Patent and Trademark Office*